(12) United States Patent
Hammerland, III

(10) Patent No.: US 11,529,186 B2
(45) Date of Patent: Dec. 20, 2022

(54) ELECTROSURGICAL FORCEPS INCLUDING THERMAL CUTTING ELEMENT

(71) Applicant: COVIDIEN LP, Mansfield, MA (US)

(72) Inventor: John A. Hammerland, III, Arvada, CO (US)

(73) Assignee: Covidien LP, Mansfield, MA (US)

( * ) Notice: Subject to any disclaimer, the term of this patent is extended or adjusted under 35 U.S.C. 154(b) by 685 days.

(21) Appl. No.: 16/518,016

(22) Filed: Jul. 22, 2019

(65) Prior Publication Data
US 2021/0022798 A1    Jan. 28, 2021

(51) Int. Cl.
*A61B 18/14* (2006.01)
*A61B 17/295* (2006.01)
(Continued)

(52) U.S. Cl.
CPC ...... *A61B 18/1442* (2013.01); *A61B 18/1445* (2013.01); *A61B 17/295* (2013.01);
(Continued)

(58) Field of Classification Search
CPC ........... A61B 2017/00353; A61B 2017/00929; A61B 2017/1125; A61B 17/28; A61B 2017/2825; A61B 2017/2926; A61B 2017/2927; A61B 2017/2929; A61B 2017/293; A61B 2017/2936; A61B 2017/2944; A61B 2018/085; A61B 2018/1442; A61B 2018/1445; A61B 2018/1447; A61B 2018/145; A61B 2018/1452; A61B 2018/1455;
(Continued)

(56) References Cited

U.S. PATENT DOCUMENTS 2,068,721 A    1/1937  Wappler
3,740,904 A    6/1973  Ainoura
(Continued)

OTHER PUBLICATIONS

Annotated_Evans_Fig_5 (Year: 2022).*
(Continued)

*Primary Examiner* — Linda C Dvorak
*Assistant Examiner* — Nicholas S Borsch
(74) *Attorney, Agent, or Firm* — Carter, DeLuca & Farrell LLP

(57) ABSTRACT

A structure of a surgical instrument configured for thermally cutting tissue. The structure includes a frame and a thermal cutting element. The frame includes a proximal flange portion and a distal body portion. The distal body portion includes a proximal section extending from the proximal flange portion, a distal section, and a center section extending between the proximal and distal sections. The distal body portion includes first and second distal body portion segments. The distal body portion segments are disposed a first distance apart from one another at the proximal section, a second distance apart from one another at the distal section, and a third distance apart from one another at the center section. The third distance is greater than the first and second distances. The thermal cutting element is disposed within the distal body portion of the frame and extends from the proximal section, through the center section, to the distal section.

10 Claims, 6 Drawing Sheets

(51) Int. Cl.
*A61B 18/08* (2006.01)
*A61B 18/00* (2006.01)
A61B 34/30 (2016.01)
A61B 17/32 (2006.01)
A61B 18/18 (2006.01)

(52) U.S. Cl.
CPC ............ *A61B 18/085* (2013.01); *A61B 34/30* (2016.02); *A61B 2017/320094* (2017.08); *A61B 2018/00083* (2013.01); *A61B 2018/00601* (2013.01); *A61B 2018/1807* (2013.01); *A61B 2018/1861* (2013.01)

(58) Field of Classification Search
CPC ............ A61B 18/1442; A61B 18/1445; A61B 18/1447; A61B 18/145; A61B 2018/1457; A61B 17/2804; A61B 2017/2808; A61B 17/2812; A61B 17/2816; A61B 17/282; A61B 17/29; A61B 2017/2938; A61B 2017/2939; A61B 2017/2947; A61B 2017/295
USPC ......................................... 606/205, 206, 207
See application file for complete search history.

(56) References Cited

U.S. PATENT DOCUMENTS

| | | |
|---|---|---|
| 4,091,813 A | 5/1978 | Shaw et al. |
| 4,984,564 A | 1/1991 | Yuen |
| 5,007,926 A | 4/1991 | Derbyshire |
| 5,037,379 A | 8/1991 | Clayman et al. |
| 5,078,726 A | 1/1992 | Kreamer |
| 5,143,082 A | 9/1992 | Kindberg et al. |
| 5,159,921 A | 11/1992 | Hoover |
| 5,171,262 A | 12/1992 | MacGregor |
| 5,176,659 A | 1/1993 | Mancini |
| 5,213,114 A | 5/1993 | Bailey, Jr. |
| 5,215,101 A | 6/1993 | Jacobs et al. |
| 5,215,521 A | 6/1993 | Cochran et al. |
| 5,224,930 A | 7/1993 | Spaeth et al. |
| 5,231,974 A | 8/1993 | Giglio et al. |
| 5,308,327 A | 5/1994 | Heaven et al. |
| 5,312,416 A | 5/1994 | Spaeth et al. |
| 5,330,483 A | 7/1994 | Heaven et al. |
| 5,354,303 A | 10/1994 | Spaeth et al. |
| 5,374,272 A | 12/1994 | Arpa et al. |
| 5,380,304 A | 1/1995 | Parker |
| 5,389,098 A | 2/1995 | Tsuruta et al. |
| 5,403,312 A | 4/1995 | Yates et al. |
| 5,411,549 A | 5/1995 | Peters |
| 5,441,515 A | 8/1995 | Khosravi et al. |
| 5,449,382 A | 9/1995 | Dayton |
| 5,465,895 A | 11/1995 | Knodel et al. |
| 5,520,610 A | 5/1996 | Giglio et al. |
| 5,578,075 A | 11/1996 | Dayton |
| 5,611,803 A | 3/1997 | Heaven et al. |
| 5,618,296 A | 4/1997 | Sorensen et al. |
| 5,636,639 A | 6/1997 | Turturro et al. |
| 5,649,550 A | 7/1997 | Crook |
| 5,707,385 A | 1/1998 | Williams |
| 5,769,794 A | 6/1998 | Conlan et al. |
| 5,785,677 A | 7/1998 | Auweiler |
| 5,810,721 A | 9/1998 | Mueller et al. |
| 5,810,811 A | 9/1998 | Yates et al. |
| 5,814,044 A | 9/1998 | Hooven |
| 5,827,271 A | 10/1998 | Buysse et al. |
| 5,833,690 A | 11/1998 | Yates et al. |
| 5,876,401 A | 3/1999 | Schulze et al. |
| 5,906,577 A | 5/1999 | Beane et al. |
| 5,911,719 A | 6/1999 | Eggers |
| 5,957,888 A | 9/1999 | Hinchliffe |
| 5,971,995 A | 10/1999 | Rousseau |
| 5,993,427 A | 11/1999 | Rolland et al. |
| 6,024,741 A | 2/2000 | Williamson, IV et al. |
| 6,027,779 A | 2/2000 | Campbell et al. |
| 6,039,748 A | 3/2000 | Savage et al. |
| 6,048,309 A | 4/2000 | Flom et al. |
| 6,059,793 A | 5/2000 | Pagedas |
| 6,086,586 A | 7/2000 | Hooven |
| 6,090,136 A | 7/2000 | McDonald et al. |
| 6,162,172 A | 12/2000 | Cosgrove et al. |
| 6,206,889 B1 | 3/2001 | Bennardo |
| 6,228,095 B1 | 5/2001 | Dennis |
| 6,258,102 B1 | 7/2001 | Pagedas |
| 6,273,887 B1 | 8/2001 | Yamauchi et al. |
| 6,350,267 B1 | 2/2002 | Stefanchik |
| 6,382,211 B1 | 5/2002 | Crook |
| 6,387,102 B2 | 5/2002 | Pagedas |
| 6,402,747 B1 | 6/2002 | Lindemann et al. |
| 6,406,440 B1 | 6/2002 | Stefanchik |
| 6,602,252 B2 | 8/2003 | Mollenauer |
| 6,736,813 B2 | 5/2004 | Yamauchi et al. |
| 6,776,780 B2 | 8/2004 | Mulier et al. |
| 6,802,843 B2 | 10/2004 | Truckai et al. |
| 6,808,525 B2 | 10/2004 | Latterell et al. |
| 6,814,700 B1 | 11/2004 | Mueller et al. |
| 6,821,273 B2 | 11/2004 | Mollenauer |
| 6,860,880 B2 | 3/2005 | Treat et al. |
| 6,899,710 B2 | 5/2005 | Hooven |
| 6,929,641 B2 | 8/2005 | Goble et al. |
| 6,953,461 B2 | 10/2005 | McClurken et al. |
| 7,011,656 B2 | 3/2006 | McGaffigan et al. |
| 7,033,356 B2 | 4/2006 | Latterell et al. |
| 7,070,597 B2 | 7/2006 | Truckai et al. |
| 7,083,619 B2 | 8/2006 | Truckai et al. |
| 7,112,201 B2 | 9/2006 | Truckai et al. |
| 7,125,409 B2 | 10/2006 | Truckai et al. |
| 7,147,637 B2 | 12/2006 | Goble |
| 7,169,146 B2 | 1/2007 | Truckai et al. |
| 7,204,835 B2 | 4/2007 | Latterell et al. |
| 7,270,664 B2 | 9/2007 | Johnson et al. |
| 7,276,068 B2 | 10/2007 | Johnson et al. |
| 7,326,202 B2 | 2/2008 | McGaffigan |
| 7,329,255 B2 | 2/2008 | McGaffigan |
| 7,354,440 B2 | 4/2008 | Truckai et al. |
| 7,357,802 B2 | 4/2008 | Palanker et al. |
| 7,364,577 B2 | 4/2008 | Wham et al. |
| 7,396,356 B2 | 7/2008 | Mollenauer |
| 7,419,490 B2 | 9/2008 | Falkenstein et al. |
| 7,547,310 B2 | 6/2009 | Whitfield |
| 7,670,346 B2 | 3/2010 | Whitfield |
| 7,686,827 B2 | 3/2010 | Hushka |
| 7,691,120 B2 | 4/2010 | Shluzas et al. |
| 7,815,641 B2 | 10/2010 | Dodde et al. |
| 7,931,649 B2 | 4/2011 | Couture et al. |
| 8,034,051 B2 | 10/2011 | Martin et al. |
| 8,075,567 B2 | 12/2011 | Taylor et al. |
| 8,162,940 B2 | 4/2012 | Johnson et al. |
| 8,187,273 B2 | 5/2012 | Kerr et al. |
| 8,197,472 B2 | 6/2012 | Lau et al. |
| 8,206,294 B2 | 6/2012 | Widenhouse et al. |
| 8,226,649 B2 | 7/2012 | Falkenstein et al. |
| 8,292,879 B2 | 10/2012 | Manwaring et al. |
| 8,303,585 B2 | 11/2012 | Mollenauer |
| 8,372,066 B2 | 2/2013 | Manwaring et al. |
| 8,377,052 B2 | 2/2013 | Manwaring et al. |
| 8,394,094 B2 | 3/2013 | Edwards et al. |
| 8,409,112 B2 | 4/2013 | Wynne et al. |
| 8,409,216 B2 | 4/2013 | Parihar et al. |
| 8,414,596 B2 | 4/2013 | Parihar et al. |
| 8,425,503 B2 | 4/2013 | Manwaring et al. |
| 8,425,533 B2 | 4/2013 | Parihar et al. |
| 8,491,578 B2 | 7/2013 | Manwaring et al. |
| 8,491,626 B2 | 7/2013 | Roy et al. |
| 8,523,850 B2 | 9/2013 | Manwaring et al. |
| 8,523,852 B2 | 9/2013 | Manwaring et al. |
| 8,540,628 B2 | 9/2013 | O'Prey et al. |
| 8,551,088 B2 | 10/2013 | Falkenstein et al. |
| 8,562,598 B2 | 10/2013 | Falkenstein et al. |
| 8,568,411 B2 | 10/2013 | Falkenstein et al. |
| 8,579,914 B2 | 11/2013 | Menn et al. |
| 8,597,180 B2 | 12/2013 | Copeland et al. |
| 8,597,293 B2 | 12/2013 | Falkenstein et al. |

(56) References Cited

U.S. PATENT DOCUMENTS

| | | |
|---|---|---|
| 8,597,297 B2 | 12/2013 | Couture et al. |
| 8,617,151 B2 | 12/2013 | Denis et al. |
| 8,623,003 B2 | 1/2014 | Lau et al. |
| 8,636,730 B2 | 1/2014 | Keppel |
| 8,734,445 B2 | 5/2014 | Johnson et al. |
| 8,777,849 B2 | 7/2014 | Haig et al. |
| 8,864,658 B2 | 10/2014 | Wilkins et al. |
| 8,915,909 B2 | 12/2014 | Manwaring et al. |
| 8,932,279 B2 | 1/2015 | Stringham et al. |
| 8,951,248 B2 | 2/2015 | Messerly et al. |
| 8,961,408 B2 | 2/2015 | Wilkins et al. |
| 8,968,329 B2 | 3/2015 | Cabrera |
| 8,986,321 B2 | 3/2015 | Parihar et al. |
| 9,005,199 B2 | 4/2015 | Beckman et al. |
| 9,017,340 B2 | 4/2015 | Davis |
| 9,039,694 B2 | 5/2015 | Ross et al. |
| 9,050,100 B2 | 6/2015 | Yates et al. |
| 9,084,606 B2 | 7/2015 | Greep |
| 9,131,977 B2 | 9/2015 | Manwaring et al. |
| 9,149,321 B2 | 10/2015 | Stringham et al. |
| 9,192,427 B2 | 11/2015 | Johnson et al. |
| 9,265,553 B2 | 2/2016 | Manwaring et al. |
| 9,265,554 B2 | 2/2016 | Manwaring et al. |
| 9,265,555 B2 | 2/2016 | Manwaring et al. |
| 9,265,556 B2 | 2/2016 | Manwaring et al. |
| 9,320,560 B2 | 4/2016 | Manwaring et al. |
| 9,387,037 B2 | 7/2016 | Yang |
| 9,402,679 B2 | 8/2016 | Ginnebaugh et al. |
| 9,579,146 B2 | 2/2017 | Johnson et al. |
| 9,877,893 B2 | 1/2018 | Taylor et al. |
| 9,918,774 B2 | 3/2018 | Batchelor et al. |
| 9,931,157 B2 | 4/2018 | Strobl et al. |
| 9,955,858 B2 | 5/2018 | Pamnani et al. |
| 10,085,794 B2 | 10/2018 | Kerr et al. |
| 10,204,773 B2 | 2/2019 | Sugiyama et al. |
| 10,213,247 B2 | 2/2019 | Manwaring et al. |
| 2005/0267492 A1 | 12/2005 | Poncet et al. |
| 2006/0200169 A1 | 9/2006 | Sniffin |
| 2006/0200170 A1 | 9/2006 | Aranyi |
| 2007/0074807 A1* | 4/2007 | Guerra .................... B29C 70/72 |
| | | 156/242 |
| 2007/0265616 A1 | 11/2007 | Couture et al. |
| 2010/0312189 A1 | 12/2010 | Shelton, IV et al. |
| 2011/0184311 A1 | 7/2011 | Parihar et al. |
| 2011/0190779 A1 | 8/2011 | Gell et al. |
| 2011/0282237 A1 | 11/2011 | Conlon |
| 2011/0319719 A1 | 12/2011 | O'Prey et al. |
| 2012/0083795 A1 | 4/2012 | Fleming et al. |
| 2012/0157777 A1 | 6/2012 | Okoniewski |
| 2013/0018411 A1* | 1/2013 | Collings .............. A61B 17/282 |
| | | 606/205 |
| 2013/0046303 A1 | 2/2013 | Evans et al. |
| 2013/0046337 A1* | 2/2013 | Evans ................ A61B 18/1445 |
| | | 606/205 |
| 2013/0123837 A1* | 5/2013 | Roy ................... A61B 18/1445 |
| | | 606/205 |
| 2013/0325025 A1 | 12/2013 | Hathaway et al. |
| 2014/0052018 A1 | 2/2014 | Hawkins |
| 2014/0135804 A1 | 5/2014 | Weisenburgh, II et al. |
| 2014/0194875 A1 | 7/2014 | Reschke et al. |
| 2015/0018825 A1* | 1/2015 | Takashino ............ A61B 18/085 |
| | | 606/52 |
| 2015/0051598 A1 | 2/2015 | Orszulak et al. |
| 2017/0156788 A1 | 6/2017 | Johnson et al. |
| 2017/0196648 A1 | 7/2017 | Ward et al. |
| 2018/0303322 A1 | 10/2018 | Pamnani et al. |
| 2019/0000538 A1 | 1/2019 | Widenhouse et al. |

OTHER PUBLICATIONS

Annotated_Evans_Fig_6B (Year: 2022).*
Annotated_Evans_Fig_6B2 (Year: 2022).*
Annotated_Takashino_Fig_12 (Year: 2022).*
Extended European Search Report issued in corresponding European Application No. 20186691.0 dated Dec. 23, 2020, 5 pages.

* cited by examiner

ELECTROSURGICAL FORCEPS INCLUDING THERMAL CUTTING ELEMENT

FIELD

The present disclosure relates to electrosurgical instruments and, more particularly, to electrosurgical forceps including thermal cutting elements to facilitate tissue treatment and/or cutting tissue.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is a structure of a surgical instrument configured for thermally cutting tissue. The structure includes a frame and a thermal cutting element. The frame includes a proximal flange portion and a distal body portion. The distal body portion includes a proximal section extending from the proximal flange portion, a distal section, and a center section extending between the proximal and distal sections. The distal body portion includes first and second distal body portion segments, wherein the distal body portion segments are disposed a first distance apart from one another at the proximal section, a second distance apart from one another at the distal section, and a third distance apart from one another at the center section. The third distance is greater than the first and second distances. The thermal cutting element is disposed within the distal body portion of the frame and extends from the proximal section, through the center section, to the distal section.

In an aspect of the present disclosure, the thermal cutting element is engaged with the distal section of the distal body portion of the frame. In such aspects, the thermal cutting element may include a fork at a distal end thereof. The fork includes first and second prongs defining a recess therebetween. The distal section of the distal body portion of the frame, in such aspects, is received within the recess with the first and second prongs on either side thereof to engage the thermal cutting element with the distal section of the distal body portion of the frame.

In another aspect of the present disclosure, the proximal flange portion of the frame includes first and second proximal flange portion segments connected to the first and second distal body portion segments, respectively. In such aspects, a proximal hub of the thermal cutting element may extend at least partially between the first and second proximal flange portion segments. Further, the proximal hub and the first and second proximal flange portion segments may define aligned apertures configured for receipt of a pivot to engage the proximal hub with the first and second proximal flange portion segments.

In another aspect of the present disclosure, a distal cap interconnects distal ends of the distal body portion segments with one another.

In still another aspect of the present disclosure, the first and third distances are substantially equal.

In yet another aspect of the present disclosure, a second frame at least partially surrounds the frame and conforms at least partially thereto.

In still yet another aspect of the present disclosure, the thermal cutting element bisects the center section of the distal body portion of the frame.

A jaw member of a surgical instrument provided in accordance with the present disclosure includes a frame, a thermal cutting element, a tissue-treating plate, and a jaw housing. The frame includes a proximal flange portion and a distal body portion including a proximal section extending from the proximal flange portion, a distal section, and a center section extending between the proximal and distal sections. The distal body portion includes first and second distal body portion segments. The distal body portion segments are disposed further apart from one another along the center section as compared to the proximal and distal sections. The thermal cutting element is disposed within the distal body portion of the structural frame and extends from the proximal section, through the center section, to the distal section. The tissue-treating plate is disposed atop the structural frame and thermal cutting element and defines a channel through which the thermal cutting element at least partially extends. The jaw housing surrounds the structural frame, the thermal cutting element, and the tissue-treating plate and retains the tissue-treating plate in position relative to the structural frame and the thermal cutting element.

The frame and/or thermal cutting element may be configured similarly as detailed above or otherwise herein. A second frame at least partially surrounding the frame and conforming at least partially thereto may likewise be provided.

In an aspect of the present disclosure, the jaw housing is formed from an insulative material and is overmolded.

In another aspect of the present disclosure, the jaw housing isolates the frame and the thermal cutting element from the tissue-treating plate.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
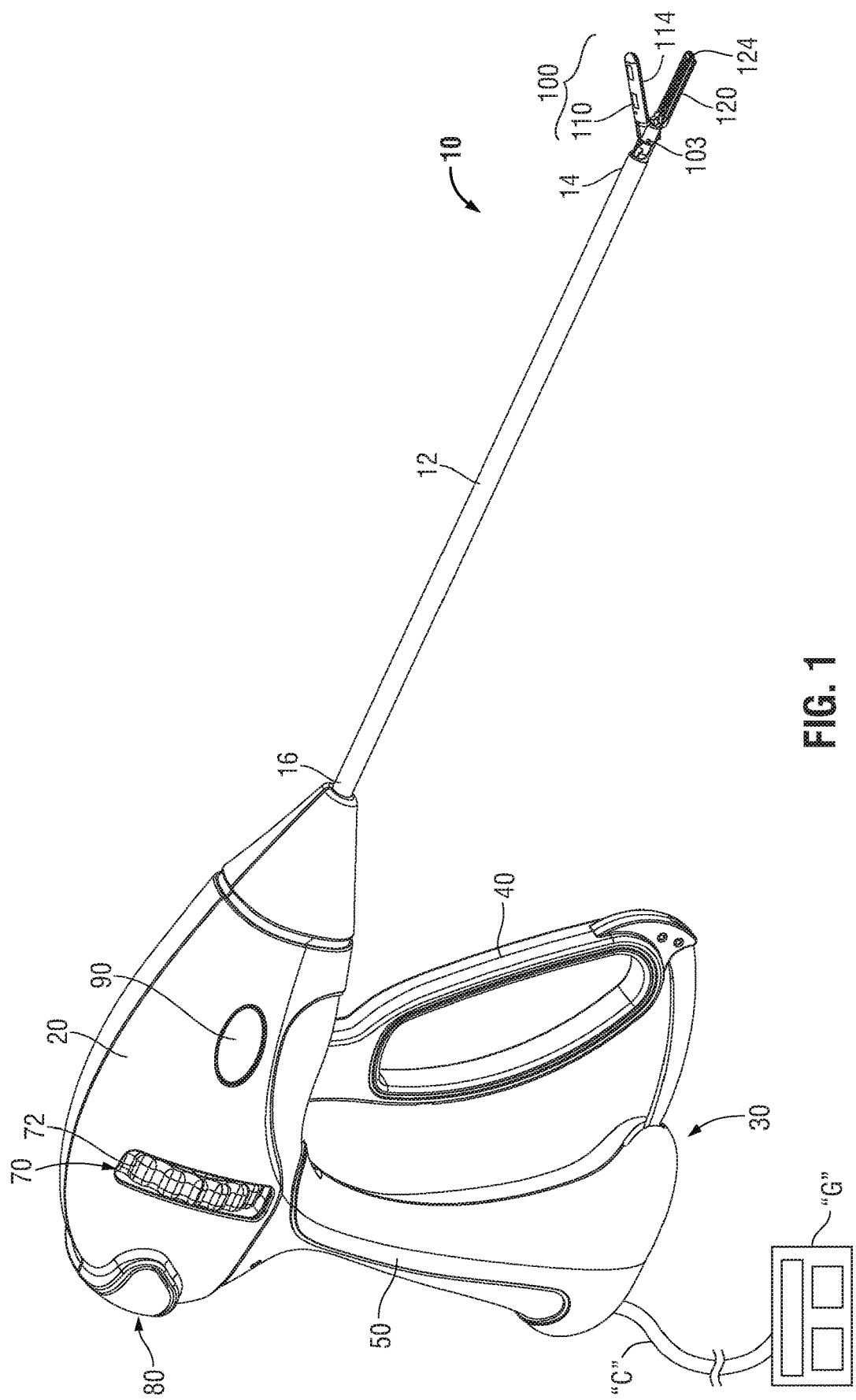
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, a first activation switch 80, a second activation switch 90, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "G." Cable "C" includes a wire (or wires) (not shown) extending therethrough that has sufficient length to extend through shaft 12 in order to connect to one or both tissue-treating surfaces 114, 124 of jaw members 110, 120, respectively, of end effector assembly 100 (see FIG. 4) to provide energy thereto. First activation switch 80 is coupled to tissue-treating surfaces 114, 124 (FIG. 4) and the electrosurgical generator "G" for enabling the selective activation of the supply of energy to jaw members 110, 120 for treating, e.g., cauterizing, coagulating/desiccating, and/or sealing, tissue. Second activation switch 90 is coupled to thermal cutting element 130 of jaw member 120 (FIG. 4) and the electrosurgical generator "G" for enabling the selective activation of the supply of energy to thermal cutting element 150 for thermally cutting tissue.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position and an approximated position to grasp tissue between tissue-treating surfaces 114, 124 of jaw members 110, 120. As shown in FIG. 1, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120. Rotating assembly 70 includes a rotation wheel 72 that is selectively rotatable in either direction to correspondingly rotate end effector assembly 100 relative to housing 20.

Figure 2:
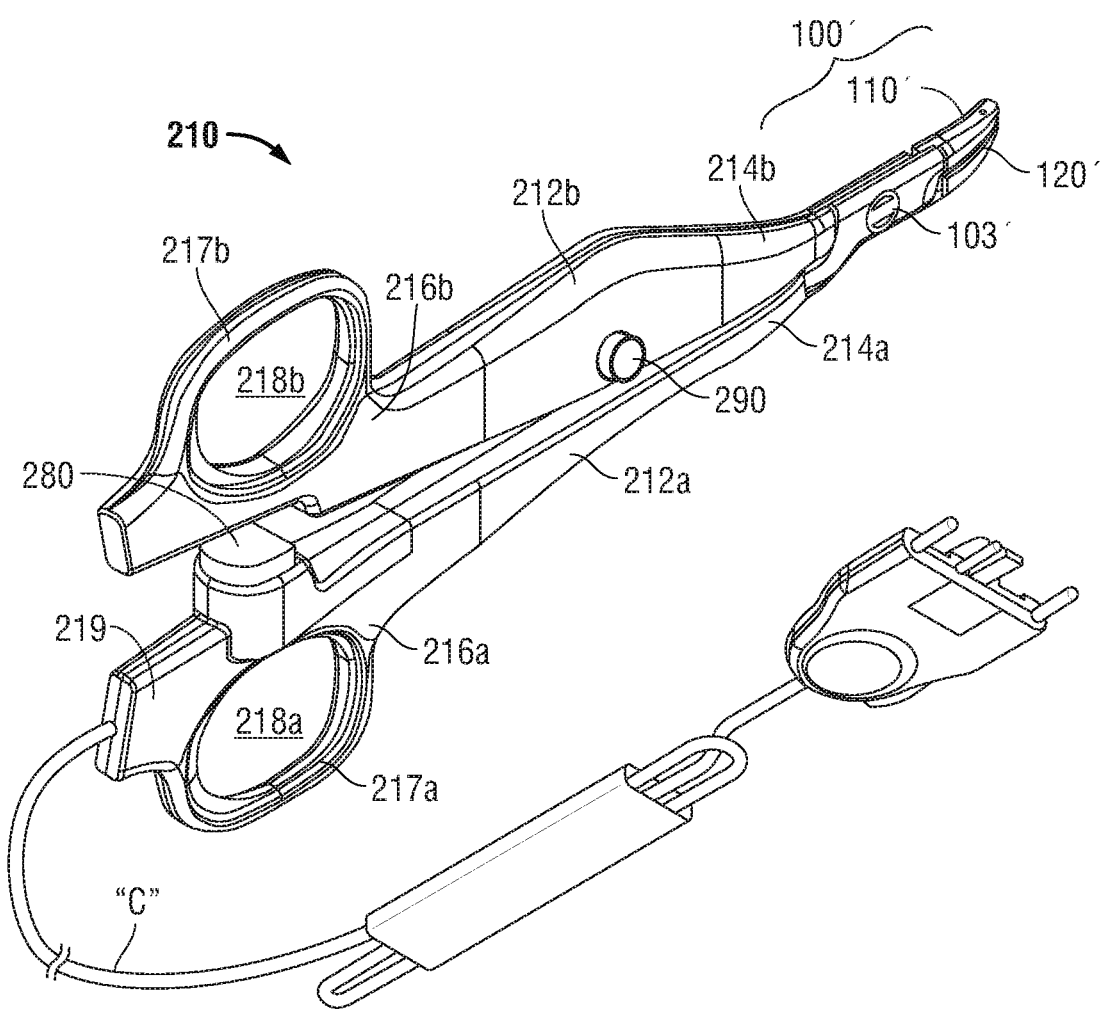
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Figure 4:
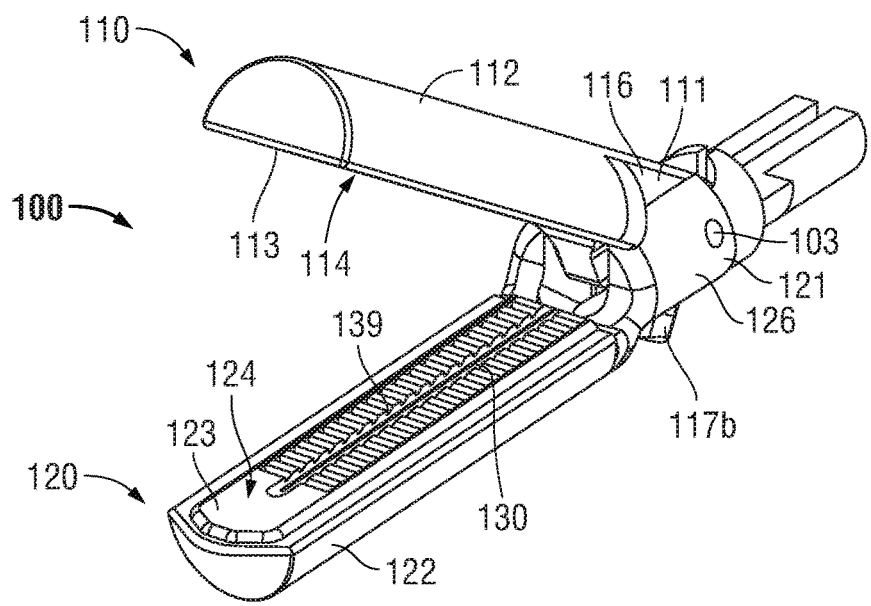
FIG. 4 is a perspective view of a distal end portion of the forceps of FIG. 1, wherein first and second jaw members of an end effector assembly of the forceps are disposed in a spaced-apart position.

Forceps 210 includes two elongated shaft members 212a, 212b, each having a proximal end portion 216a, 216b, and a distal end portion 214a, 214b, respectively. Forceps 210 is configured for use with an end effector assembly 100' similar to end effector assembly 100 (FIG. 4). More specifically, end effector assembly 100' includes first and second jaw members 110', 120' attached to respective distal end portions 214a, 214b of shaft members 212a, 212b. Jaw members 110', 120' are pivotably connected about a pivot 103'. Each shaft member 212a, 212b includes a handle 217a, 217b disposed at the proximal end portion 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 212a, 212b of forceps 210, e.g., shaft member 212b, includes a proximal shaft connector 219 configured to connect forceps 210 to a source of energy, e.g., electrosurgical generator "G" (FIG. 1). Proximal shaft connector 219 secures a cable "C" to forceps 210 such that the user may selectively supply energy to jaw members 110', 120' for treating tissue. More specifically, a first activation switch 280 is provided for supplying energy to jaw members 110', 120' to treat tissue upon sufficient approximation of shaft members 212a, 212b, e.g., upon activation of first activation switch 280 via shaft member 212a. A second activation switch 290 disposed on either or both of shaft members 212a, 212b is coupled to the thermal cutting element (not shown, similar to thermal cutting element 150 of jaw member 120 (FIG. 4)) of one of the jaw members 110', 120' of end effector assembly 100' and to the electrosurgical generator "G" for enabling the selective activation of the supply of energy to the thermal cutting element for thermally cutting tissue.

Jaw members 110', 120' define a curved configuration wherein each jaw member is similarly curved laterally off of a longitudinal axis of end effector assembly 100'. However, other suitable curved configurations including curvature towards one of the jaw members 110, 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
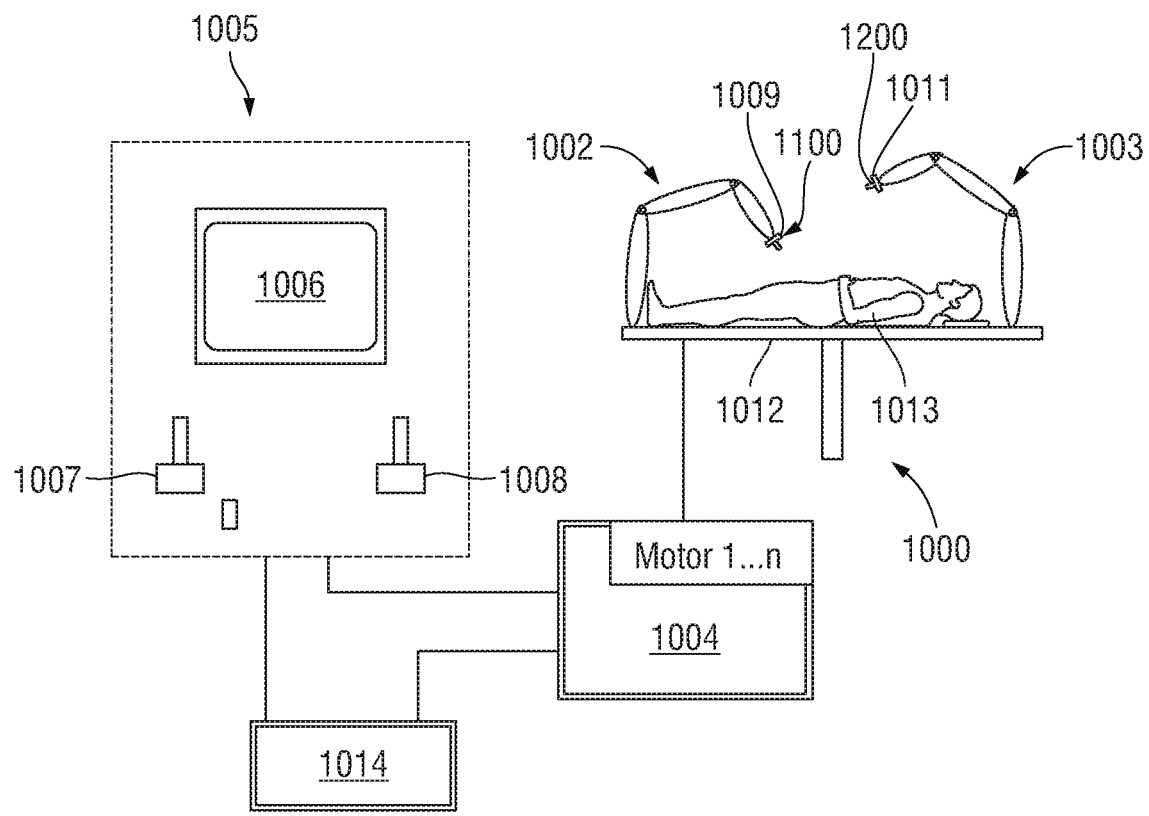
FIG. 3 is a schematic illustration of a robotic surgical instrument provided in accordance with the present disclosure.

Referring to FIG. 3, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical instrument 1000 may be configured for use on a patient 1013 lying on a patient table 1012 to be treated in a minimally invasive manner Robotic surgical instrument 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to end effector assembly 100 (FIG. 4), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 5A:
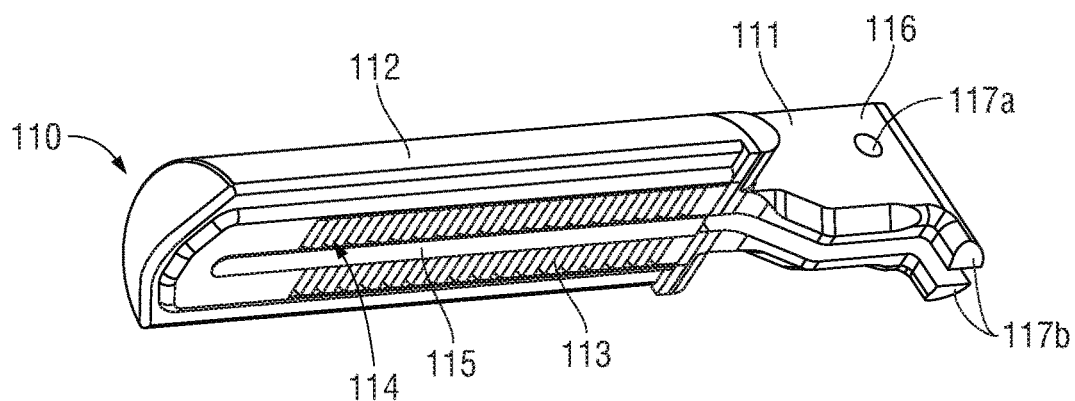
FIG. 5A is a bottom, perspective view of the first jaw member of the end effector assembly of FIG. 4.
Figure 5B:
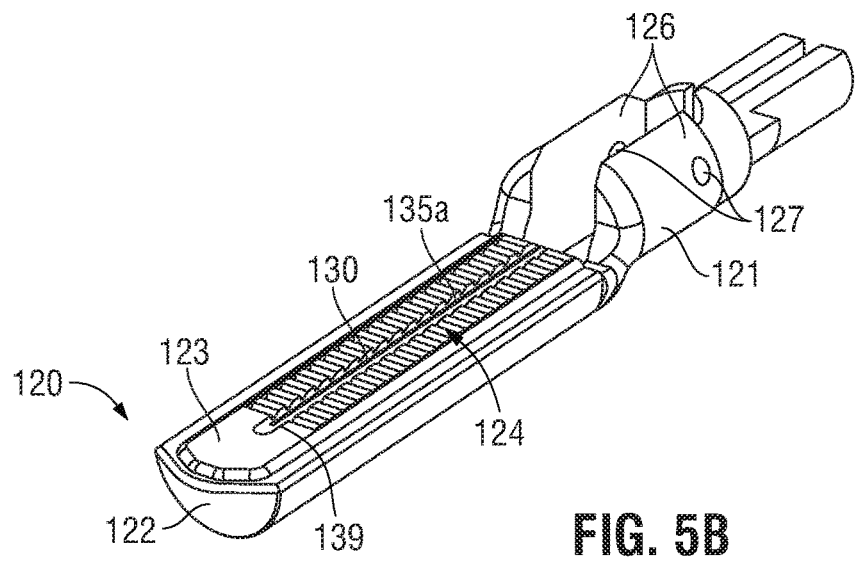
FIG. 5B is a top, perspective view of the second jaw member of the end effector assembly of FIG. 4.

Turning to FIGS. 4-5B, end effector assembly 100, as noted above, includes first and second jaw members 110, 120. Each jaw member 110, 120 may include a structural frame 111, 121, a jaw housing 112, 122, and a tissue-treating plate 113, 123 defining the respective tissue-treating surface 114, 124 thereof. Alternatively, only one of the jaw members, e.g., jaw member 120, may include a structural frame 121, jaw housing 122, and tissue-treating plate 123 defining the tissue-treating surface 124. In such embodiments, the other jaw member, e.g., jaw member 110, may be formed as a single unitary body, e.g., a piece of conductive material acting as the structural frame 111 and jaw housing 112 and defining the tissue-treating surface 114. An outer surface of the jaw housing 112, in such embodiments, may be at least partially coated with an insulative material or may remain exposed.

Referring in particular to FIGS. 4 and 5A, jaw member 110, as noted above, may be configured similarly as jaw member 120, may be formed as a single unitary body, or may be formed in any other suitable manner so as to define a tissue-treating surface 114 opposing tissue-treating surface 124 of jaw member 120 and a structural frame 111. Structural frame 111 includes a proximal flange portion 116 about which jaw member 110 is pivotably coupled to jaw member 120. In shaft-based or robotic embodiments, proximal flange portion 116 may further include an aperture 117a for receipt of pivot 103 and at least one protrusion 117b extending therefrom that is configured for receipt within an aperture defined within a drive sleeve of the drive assembly (not shown) such that translation of the drive sleeve, e.g., in response to actuation of movable handle 40 (FIG. 1) or a robotic drive, pivots jaw member 110 about pivot 103 and relative to jaw member 120 between the spaced-apart position and the approximated position. However, other suitable drive arrangements are also contemplated, e.g., using cam pins and cam slots, a screw-drive mechanism, etc.

Regardless of the particular configuration of jaw member 110, jaw member 110 further includes a longitudinally-extending insulative member 115 extending along at least a portion of the length of tissue-treating surface 114. Insulative member 115 may be transversely centered on tissue-treating surface 114 or may be offset relative thereto. Further, insulative member 115 may be disposed, e.g., deposited, coated, etc., on tissue-treating surface 114, may be positioned within a channel or recess defined within tissue-treating surface 114, or may define any other suitable configuration. Additionally, insulative member 115 may be substantially (within manufacturing, material, and/or use tolerances) coplanar with tissue-treating surface 114, may protrude from tissue-treating surface 114, may be recessed relative to tissue-treating surface 114, or may include different portions that are coplanar, protruding, and/or recessed relative to tissue-treating surface 114. Insulative member 115 may be formed from, for example, ceramic, parylene, nylon, PTFE, or other suitable material(s) (including combinations of insulative and non-insulative materials).

Figure 6:
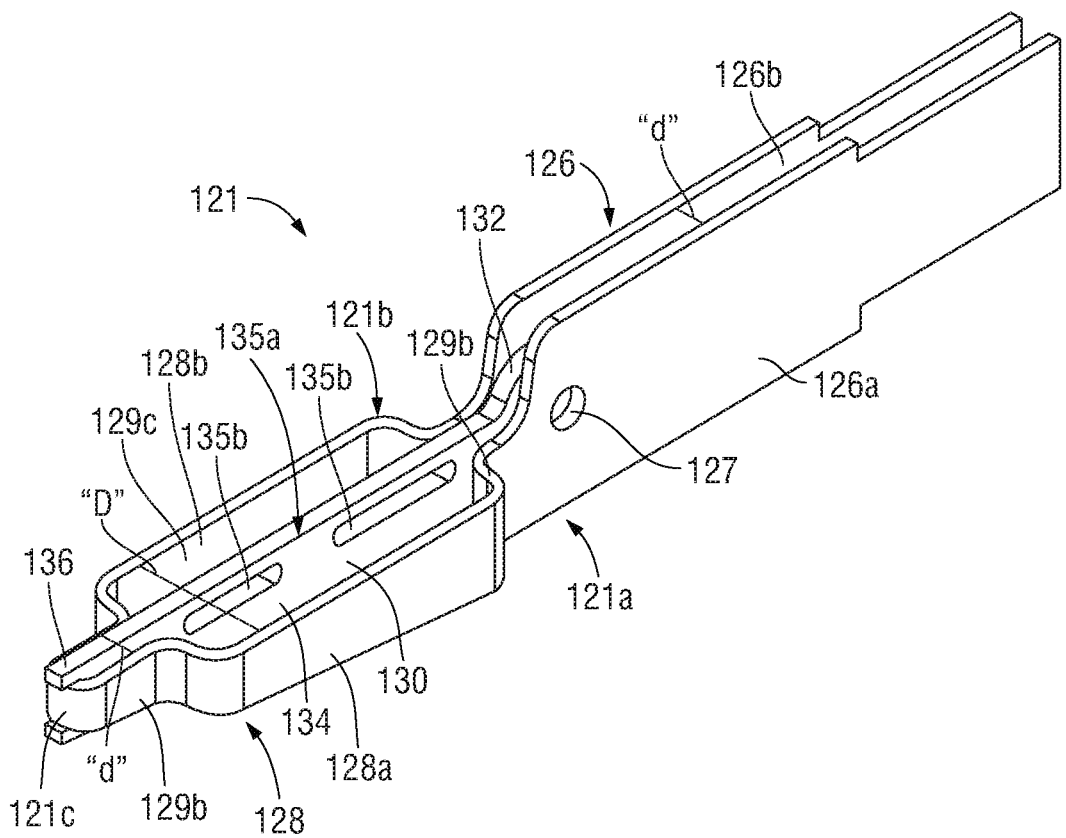
FIG. 6 is a perspective view of a structural frame and thermal cutting element of the second jaw member of the end effector assembly of FIG. 4.
Figure 7:
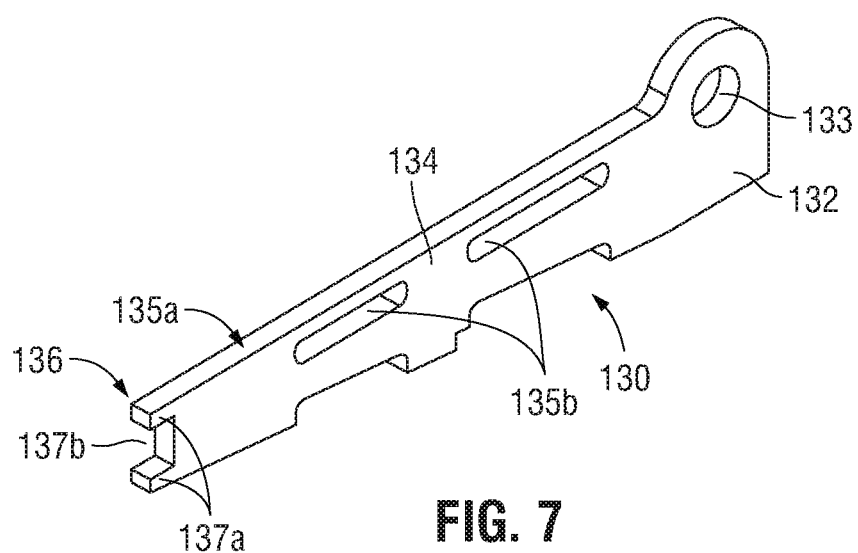
FIG. 7 is a perspective view of the thermal cutting element of FIG. 6.

With reference to FIGS. 4, 5B, and 6, as noted above, jaw member 120 includes a structural frame 121, a jaw housing 122, and a tissue-treating plate 123 defining the tissue-treating surface 124 thereof. Jaw member 120 further include a thermal cutting element 130 mounted thereon. Structural frame 121 may be formed as a vertically-oriented plate including first and second longitudinally-extending segments 121a, 121b connected to one another at a distal tip 121c of structural frame 121. Structural frame 121 may be formed form a single, monolithic plate of material, e.g., stainless steel, titanium, or other suitable material bent to define the various features thereof, or may include multiple plates or other pieces of material joined to one another.

Structural frame 121 defines a proximal flange portion 126 and a distal body portion 128 extending distally from proximal flange portion 126. More specifically, first and second longitudinally-extending segments 121a, 121b each include a proximal flange portion segment 126a, 126b (collectively proximal flange portion 126) and a distal body portion segment 128a, 128b (collectively distal body portion 128). Proximal flange portion segments 128a, 128b are spaced-apart, substantially parallel, and define aligned apertures 127 configured for receipt of pivot 103 therethrough to pivotably couple jaw members 110, 120 with one another.

Distal body portion segments 128a, 128b of distal body portion 128 extend distally from proximal flange portion segments 126a, 126b, respectively. Distal body portion 128 defines a proximal end 129a where distal body portion segments 128a, 128b are connected with proximal flange portion segments 126a, 126b, a distal end 129b where distal body segments 128a, 128b are connected with one another to define distal tip 121c, and a center section 129c extending between proximal and distal ends 129a, 129b, respectively. Center section 129c extends at least a majority of the length of distal body portion 128. Distal body portion segments 128a, 128b define a substantially (within manufacturing, material, and/or use tolerances) constant, maximum transverse distance "D" therebetween along center section 129c, converge towards one another at proximal end 129a to meet proximal flange portion segments 126a, 126b which are disposed a closer transverse distance "d" from one another, and converge towards one another at distal end 129b to define distal tip 121c. As illustrated in FIG. 6, distal tip 121c may include a pair of longitudinal segments transversely-spaced the distance "d" from one another and a distal cap connecting the longitudinal segments, although other configurations are also contemplated.

Thermal cutting element 130, as illustrated in FIGS. 4, 5B, 6, and 7, defines a vertically-oriented plate including a proximal hub 132, a center body 134, and a distal fork 136. Proximal hub 132 is configured for positioning between proximal flange portion segments 126a, 126b of proximal flange portion 126 of structural frame 121 and defines an aperture 133 aligned with apertures 127 of proximal flange portion 126 of structural frame 121 to likewise receive pivot 103 therethrough. In this manner, thermal cutting element 130 is substantially fixed relative to structural frame 121 at the proximal end of thermal cutting element 130. Proximal hub 132 may define a thickness substantially (within manufacturing, material, and/or use tolerances) equal to the distance "d" defined between proximal flange portion segments 126a, 126b or a thickness slightly less than, e.g., at least 85% of, the distance "d" defined between proximal flange portion segments 126a, 126b, although other thicknesses are also contemplated.

Center body 134 of thermal cutting element 130 extends distally from proximal hub 132 through center section 129c of distal body portion 128 of structural frame 121. Center body 134 may bisect center section 129c of distal body portion 128 such that center body 134 extends through center section 129c while transversely spaced from each of the distal body portion segments 128a, 128b a distance equal to one half of the maximum distance "D." With this configuration, and due to the fact that center section 129c extends at least a majority of the length of distal body portion 128 of structural frame 121, structural frame 121 and thermal cutting element 130 are maximally spaced-apart (a distance equal one half of the maximum distance "D") over the majority of the lengths thereof and only contact or closely approximate one another at the respective ends thereof. Alternatively, instead of center body 134 equally bisecting center section 129c, center body 134 may be offset to one side or the other, e.g., in embodiments, up to 5% offset, 10% offset, 15% offset, etc.

Center body 134 of thermal cutting element 130 defines an upper, tissue-treating surface 135a which may be flat, angles, pointed, curved, or include any suitable configuration. Center body portion 134 may further include one or more transverse slots 135b defined therethrough to reduce the thermal mass and, thus, facilitate cooling of thermal cutting element 130. Alternatively or additionally, transverse slots 135b enable penetration of a portion of jaw housing 122 therethrough to facilitate retention of thermal cutting element 130 and structural frame 121, e.g., via one or more overmolding shots.

Distal fork 136 of thermal cutting element 130 defines a pair of vertically-spaced prongs 137a defining a recess 137b therebetween. Recess 137b is configured to receive distal tip 121c of structural frame 121 with prongs 137a disposed on either side thereof, e.g., above and below distal tip 121c. In this manner, thermal cutting element 130 is substantially fixed relative to structural frame 121 at the distal end of thermal cutting element 130 and, as noted above, only contacts or closely approximates structural frame 121 at the respective ends thereof. As an alternative to fork-recess engagement, other suitable engagement are also contemplated, e.g., a tab-slot engagement.

In embodiments where end effector assembly 100, or a portion thereof, is curved, structural frame 121 and thermal cutting element 130, or corresponding portions thereof, may similarly be curved, e.g., wherein structural frame 121 and thermal cutting element 130 (or corresponding portions thereof) are relatively configured with reference to an arc (or arcs) of curvature rather than a longitudinal axis. Thus, the terms longitudinal, transverse, and the like as utilized herein are not limited to linear configurations, e.g., along linear axes, but apply equally to curved configurations, e.g., along arcs of curvature.

Referring back to FIG. 5B, in conjunction with FIG. 6, jaw housing 122 may be formed from an electrically-insulative material and includes one or more portions (separate or unitary) formed in any suitable manner such as, for example, via overmolding. More specifically, in embodiments, a first overmold may capture structural frame 121 and cutting element 130 while a second overmold captures tissue-treating plate 113, the first overmold, structural frame 121, and cutting element 130 to maintain plate 113 isolated from frame 121 and element 130. Alternatively, only the second overmold may be provided to capture tissue-treating plate 113, structural frame 121, and cutting element 130 (while still maintaining the isolation therebetween). As another alternative, an insulative insert may form a portion of jaw housing 122 together with or in place of either or both overmolds. The insulative material, in any of the above configurations, may fill only a portion of the interior of jaw member 120 such that the interior is at least partially hollow, or may fill the substantial entirety of the interior of jaw member 120. Other suitable configurations are also contemplated.

Regardless of the particular configuration of jaw housing 122, the assembled jaw member 120 includes tissue-treating plate 123 defining tissue-treating surface 124 and tissue-treating surface 135a of thermal cutting element 130 substantially (within manufacturing, material, and/or use tolerances) coplanar with tissue-treating surface 124, protruding from tissue-treating surface 124, recessed relative to tissue-treating surface 124, or provided in any other suitable manner. Tissue-treating plate 123, more specifically, may define a channel 139 through which thermal cutting element 130 at least partially extends such that tissue-treating surface 135a thereof is exposed. The remainder of channel 139 may be filled with an insulative material, e.g., a portion jaw housing 122 or other insulator, to isolate thermal cutting element 130 from tissue-treating plate 123. With additional reference to FIG. 5A, in the closed position of jaw members 110, 120, tissue-treating surface 135a of cutting element 130 is configured to oppose insulative member 115 to isolate thermal cutting element 130 from tissue-treating plate 113.

Generally referring to FIGS. 1-7, tissue-treating plates 113, 123 are formed from an electrically conductive material, e.g., for conducting electrical energy therebetween for treating tissue, although tissue-treating plates 113, 123 may alternatively be configured to conduct any suitable energy, e.g., thermal, microwave, light, ultrasonic, etc., through tissue grasped therebetween for energy-based tissue treatment. As mentioned above, tissue-treating plates 113, 123 are coupled to activation switch 80 and electrosurgical generator "G" (FIG. 1) such that energy may be selectively supplied to tissue-treating plates 113, 123 and conducted therebetween and through tissue disposed between jaw members 110, 120 to treat tissue, e.g., seal tissue on either side and extending across of thermal cutting element 130.

Thermal cutting element 130, on the other hand, is configured to connect to electrosurgical generator "G" (FIG. 1) and second activation switch 90 to enable selective activation of the supply of energy to thermal cutting element 130 for heating thermal cutting element 130 to thermally cut tissue disposed between jaw members 110, 120, e.g., to cut the sealed tissue into first and second sealed tissue portions. Other configurations including multi-mode switches, other separate switches, etc. may alternatively be provided.

Thermal cutting element 130 may be any suitable thermal cutting element such as, for example, an aluminum substrate that is Plasma Electrolytic Oxidation (PEO)-treated at least along a portion of tissue-treating surface 135a such that when an AC voltage is applied, the PEO-treated portion thereof is heated for thermally cutting tissue. As another example, thermal cutting element 130 may be configured as a ferromagnetic (FM) element including a core, e.g., copper, and a ferromagnetic material coated on the core such that when an AC voltage is applied, the FM element is heated up to the Curie point (thus providing automatic, Curie-point temperature control) for thermally cutting tissue. Other suitable cutting element configurations are also contemplated. The above-detailed configuration of structural frame 121 of jaw member 120 and thermal cutting element 130, e.g., wherein there is minimal contact or approximation therebetween (only at the proximal and distal ends of thermal cutting element 130) and where free space or insulator is otherwise disposed therebetween, reduces thermal heating of structural frame 121 of jaw member 120 when thermal cutting element 130 is heated (by reducing the conductive pathways for heat to travel to structural frame 121), thus helping to reduce the overall temperature of jaw member 120 and facilitate cooling after use.

Figure 8:
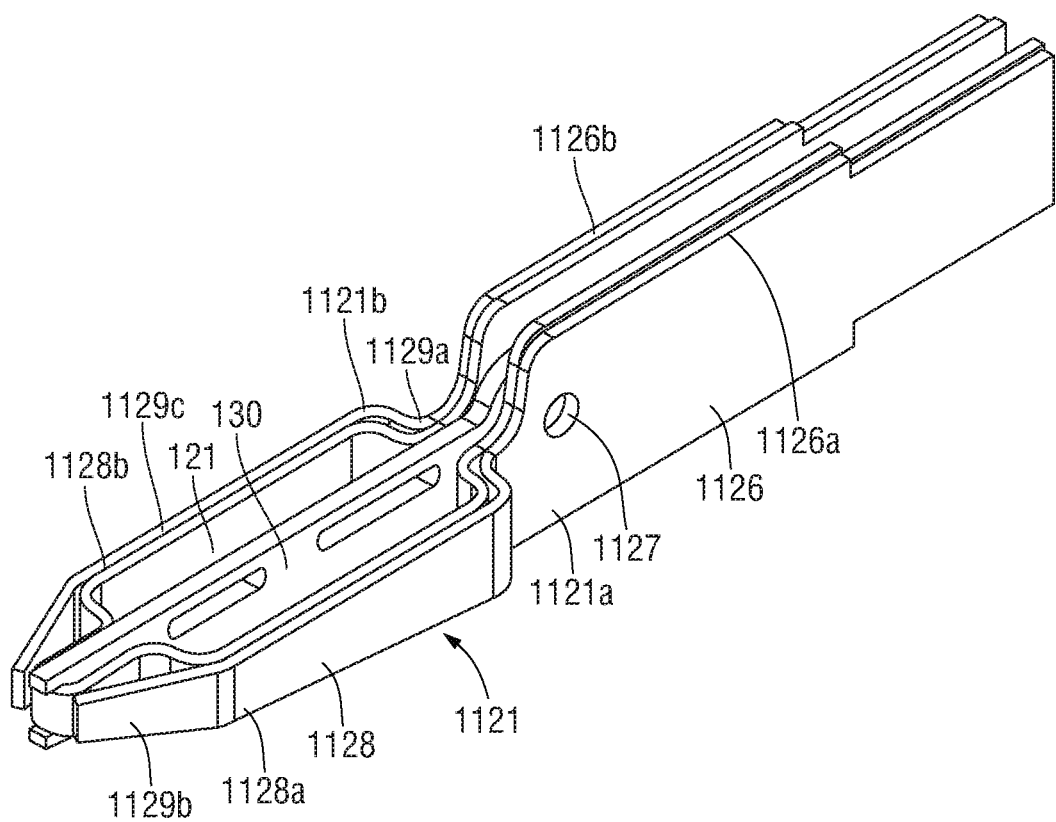
FIG. 8 is a perspective view of the structural frame and thermal cutting element of the second jaw member of the end effector assembly of FIG. 4 including an additional frame structure.

Turning to FIG. 8, in embodiments, a second structural frame 1121 may be provide in addition to (the first) structural frame 121. Second structural frame 1121 defines a proximal flange portion 1126 and a distal body portion 1128 extending distally from proximal flange portion 1126. More specifically, first and second longitudinally-extending segments 1121a, 1121b each include a proximal flange portion segment 1126a, 1126b (collectively proximal flange portion 1126) and a distal body portion segment 1128a, 1128b (collectively distal body portion 1128). Proximal flange portion segments 1126a, 1126b are spaced-apart, substantially parallel, and define aligned apertures 1127 (only the aperture 1127 of proximal flange segment 1126a is shown) configured for receipt of pivot 103 (FIG. 4) therethrough.

Distal body portion segments 1128a, 1128b of distal body portion 1128 extend distally from proximal flange portion 1126a, 1126b, respectively. Distal body portion 1128 defines a proximal end 1129a where distal body portion segments 1128a, 1128b are connected with proximal flange portion segments 1126a, 1126b, a distal end 1129b where distal body segments 1128a, 1128b define free ends spaced-apart from one another at distal tip 121c of first structural frame 121.

Second structural frame 1121 surrounds the perimeter of and generally conforms to the configuration of first structural frame 121, except for the distal ends thereof although, in embodiments, the distal end of second structural frame 1121 may likewise track the configuration of the distal end of first structural frame 121. Second structural frame 1121 may be spaced-apart from first structural frame 121 entirely or along portions thereof and any space therebetween may be vacant or at least partially filled, e.g., with insulative material from an overmold or otherwise provided. Second structural frame 1121 may be captured relative to first structural frame 121 and/or the other components of jaw member 120 via an overmold or in any other suitable manner. Second structural frame 1121 provides increased structural support to jaw member 120 (FIGS. 4 and 5B) while still reducing thermal heating of jaw member 120, thus helping to reduce the overall temperature of jaw member 120 and facilitate cooling after use.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A jaw member of a surgical instrument, comprising:
   a frame including a proximal flange portion and a distal body portion, the distal body portion including a proximal section extending from the proximal flange portion, a distal section, and a center section extending between the proximal and distal sections, the distal body portion including first and second distal body portion segments, wherein the distal body portion segments are disposed further apart from one another along the center section as compared to the proximal and distal sections;
   a thermal cutting element disposed within the distal body portion of the structural frame and extending from the proximal section, through the center section, to the distal section;
   a tissue-treating plate disposed atop the structural frame and thermal cutting element, the tissue-treating plate defining a channel, wherein a tissue-treating surface of the thermal cutting element extends at least partially through the channel; and
   a jaw housing surrounding the structural frame, the thermal cutting element, and the tissue-treating plate and retaining the tissue-treating plate in position relative to the structural frame and the thermal cutting element,
   wherein the thermal cutting element is engaged with the distal section of the distal body portion of the frame, and
   wherein the thermal cutting element includes a fork at a distal end thereof, the fork including first and second prongs defining a recess therebetween, wherein the distal section of the distal body portion of the frame is received within the recess with the first and second prongs on either side thereof to engage the thermal cutting element with the distal section of the distal body portion of the frame.

2. The jaw member according to claim 1, wherein the proximal flange portion of the frame includes first and second proximal flange portion segments connected to the first and second distal body portion segments, respectively.

3. The jaw member according to claim 2, wherein a proximal hub of the thermal cutting element extends at least partially between the first and second proximal flange portion segments.

4. The jaw member according to claim 3, wherein the proximal hub and the first and second proximal flange portion segments define aligned apertures configured for receipt of a pivot to engage the proximal hub with the first and second proximal flange portion segments.

5. The jaw member according to claim 1, wherein a distal tip interconnects distal ends of the distal body portion segments with one another.

6. The jaw member according to claim 1, further comprising a second frame at least partially surrounding the frame and conforming at least partially thereto.

7. The jaw member according to claim 1, wherein the jaw housing is formed from an insulative material and is overmolded.

8. The jaw member according to claim 1, wherein the jaw housing isolates the frame and the thermal cutting element from the tissue-treating plate.

9. A jaw member of a surgical instrument, comprising:
a frame including a proximal flange portion and a distal body portion, the distal body portion including a proximal section extending from the proximal flange portion, a distal section, and a center section extending between the proximal and distal sections, the distal body portion including first and second distal body portion segments, wherein the distal body portion segments are disposed further apart from one another along the center section as compared to the proximal and distal sections;
a thermal cutting element disposed within the distal body portion of the frame and extending from the proximal section, through the center section, to the distal section;
a tissue-treating plate disposed atop the frame and thermal cutting element, the tissue-treating plate defining a channel, wherein a tissue-treating surface of the thermal cutting element extends at least partially through the channel; and
a jaw housing surrounding the structural frame, the thermal cutting element, and the tissue-treating plate and retaining the tissue-treating plate in position relative to the frame and the thermal cutting element,
wherein the proximal flange portion of the frame includes first and second proximal flange portion segments connected to the first and second distal body portion segments, respectively, and
wherein a proximal hub of the thermal cutting element extends at least partially between the first and second proximal flange portion segments, and
wherein the proximal hub and the first and second proximal flange portion segments define aligned apertures configured for receipt of a pivot to engage the proximal hub with the first and second proximal flange portion segments.

10. A jaw member of a surgical instrument, comprising:
a frame including a proximal flange portion and a distal body portion, the distal body portion including a proximal section extending from the proximal flange portion, a distal section, and a center section extending between the proximal and distal sections, the distal body portion including first and second distal body portion segments, wherein the distal body portion segments are disposed further apart from one another along the center section as compared to the proximal and distal sections;
a thermal cutting element disposed within the distal body portion of the frame and extending from the proximal section, through the center section, to the distal section;
a tissue-treating plate disposed atop the frame and thermal cutting element, the tissue-treating plate defining a channel, wherein a tissue-treating surface of the thermal cutting element extends at least partially through the channel;
a jaw housing surrounding the frame, the thermal cutting element, and the tissue-treating plate and retaining the tissue-treating plate in position relative to the frame and the thermal cutting element; and
a second frame at least partially surrounding the frame and conforming at least partially thereto.

\* \* \* \* \*